(12) United States Patent
Jalde

(10) Patent No.: US 6,564,798 B1
(45) Date of Patent: May 20, 2003

(54) METHOD AND COMPUTER SOFTWARE PRODUCT FOR CONTROLLING AN EXPIRATORY VALVE IN A VENTILATOR

(75) Inventor: Fredrik Jalde, Stockholm (SE)

(73) Assignee: Siemens Elema AB, Solna (SE)

( * ) Notice: Subject to any disclaimer, the term of this patent is extended or adjusted under 35 U.S.C. 154(b) by 148 days.

(21) Appl. No.: 09/616,280

(22) Filed: Jul. 14, 2000

(30) Foreign Application Priority Data

Jul. 15, 1999 (SE) ................................................ 9902709

(51) Int. Cl.7 ................................................ A62B 9/62
(52) U.S. Cl. ............................ 128/205.24; 128/204.18; 128/200.24
(58) Field of Search ................. 128/205.24, 204.18, 128/204.21, 204.23, 200.24

(56) References Cited

U.S. PATENT DOCUMENTS

| | | | | |
|---|---|---|---|---|
| 4,611,591 A | * | 9/1986 | Inui et al. | 128/204.21 |
| 5,002,050 A | * | 3/1991 | McGinnis | 128/204.18 |
| 5,072,729 A | * | 12/1991 | DeVries | 128/204.23 |
| 5,323,772 A | * | 6/1994 | Linden et al. | 128/204.23 |
| 5,373,842 A | * | 12/1994 | Olsson et al. | 128/204.21 |
| 5,390,666 A | * | 2/1995 | Kimm et al. | 128/204.26 |
| 5,540,220 A | * | 7/1996 | Gropper et al. | 128/204.23 |
| 5,575,283 A | * | 11/1996 | Sjoestrand | 128/204.18 |
| 5,582,163 A | * | 12/1996 | Bonassa | 128/204.26 |
| 5,647,351 A | * | 7/1997 | Weismann et al. | 128/204.21 |
| 5,692,497 A | * | 12/1997 | Schnitzer et al. | 128/204.18 |
| 5,797,393 A | * | 8/1998 | Kohl | 128/204.23 |
| 5,813,399 A | * | 9/1998 | Isaza et al. | 128/204.21 |
| 5,931,162 A | * | 8/1999 | Christian | 128/204.23 |
| 6,119,686 A | * | 9/2000 | Somerson et al. | 128/202.22 |
| 6,192,885 B1 | * | 2/2001 | Jalde | 128/204.18 |
| 6,257,234 B1 | * | 7/2001 | Sun | 128/204.18 |
| 6,279,574 B1 | * | 8/2001 | Richardson et al. | 128/204.17 |
| 6,305,374 B1 | * | 10/2001 | Zdrojkowski et al. | 128/204.21 |
| 6,345,619 B1 | * | 2/2002 | Finn | 128/204.18 |
| 6,347,630 B1 | * | 2/2002 | Takahashi et al. | 128/204.18 |
| 6,390,091 B1 | * | 5/2002 | Banner et al. | 128/204.21 |
| 6,439,229 B1 | * | 8/2002 | Du et al. | 128/204.23 |

FOREIGN PATENT DOCUMENTS

| | | |
|---|---|---|
| DE | 293 268 | 8/1991 |
| EP | 0 903 159 | 3/1999 |
| EP | 0 965 357 | 12/1999 |

* cited by examiner

Primary Examiner—Weilun Lo
Assistant Examiner—Teena Mitchell
(74) Attorney, Agent, or Firm—Schiff & Hardin & Waite

(57) ABSTRACT

In a method for controlling an expiratory valve in a ventilator during expiration, including a stage in which the expiratory valve is opened almost completely for a first interval. Opening the expiratory valve almost completely results in a reduction in expiratory resistance. Thus in the first interval of flow or pressure in the expiratory part of the ventilator, a determination is made when the flow or pressure in the expiratory part meets a condition. A second interval is started when the flow in the expiratory part meets the condition and the expiratory valve is regulated during the second interval in order to attain a pre-set end pressure in the expiratory section.

6 Claims, 3 Drawing Sheets

METHOD AND COMPUTER SOFTWARE PRODUCT FOR CONTROLLING AN EXPIRATORY VALVE IN A VENTILATOR

BACKGROUND OF THE INVENTION

1. Field of the Invention

The present invention is directed to a method for controlling an expiratory valve in a ventilator and to a computer software product operating in accordance with the invention.

2. Description of the Prior Art

In normal circumstances during respiratory care, the patient must be allowed to exhale in as normally as possible, sometimes against an elevated end expiratory pressure (PEEP). The tubing (the tracheal tube in particular) and devices (e.g. dehumidifier and bacterial filter but especially the ventilator's expiratory valve) located in the path of flow of expired gas then pose resistance to expiration. The patient is forced to overcome this unnatural resistance, which may be arduous for the patient.

One way to reduce this resistance is to open the expiratory valve to the maximum for a specific period. East German Patent 293 268 describes one such regulatory procedure for a ventilator. In this known procedure, the expiratory valve is an ON/OFF valve with only two positions, completely open or completely closed.

This known regulation of the expiratory valve is accomplished by opening the expiratory valve at the start of expiration. It is then kept open a certain amount of time and then closed. The pressure (end pressure) then present at the valve (on the patient side) corresponds to the pressure in the patient's lungs. The time the valve should be kept open is determined for subsequent breathing cycles from the difference between the actual end pressure obtained (actual value) and a pre-set pressure for PEEP (reference value). If the actual value is greater than the reference value, the time the valve is kept open is increased. If the actual value is less than the reference value, the time the valve is kept open is reduced. Adjustment toward the reference value is achieved in this manner.

One disadvantage of this known regulatory system is that the patient runs the risk of being subjected to an end pressure lower than PEEP during the initial phase of treatment (when maintaining PEEP is particularly important in preventing the collapse of alveoli in the lungs).

Another disadvantage of this known regulatory system is that the patient is subjected to a varying end pressure, at least during the adjustment phase, since an end pressure higher than the desired PEEP also could be obtained.

A further disadvantage of this known regulatory system is that the patient's lungs, plus the tubing, does not constitute a static system. Any change in the patient's position could change the parameters of the gas mechanics of the lungs/tubing system, and the regulatory system would not be able to compensate for this. In a worst case scenario, this could lead to an end pressure far lower (or higher) than the reference value.

Yet another disadvantage is that basic flows cannot be employed, since the known valve is an ON/OFF valve. Basic flows have the advantage of making flow triggering possible for the patient.

Many of these disadvantages can be resolved with a method described in European Application 965 357 (published after the priority date of the present application). This method divides expiration into two phases. In the first phase, the valve is opened enough to reduce flow resistance considerably. In the second phase, the valve is regulated toward the correct end pressure. The duration of the first phase is determined from parameters obtained during the second phase or at the transition between the two phases.

One phenomenon that can, in practice, make it hard to keep an expiratory valve completely open during the first phase (in order to minimize resistance to flow) is that the duration of the second phase becomes too short to allow establishment of the correct end pressure (PEEP). If, in addition, the expiratory valve is non-linear, this could have an adverse impact on regulation in the second phase.

SUMMARY OF THE INVENTION

An object of the present invention is to provide a method that avoids the aforementioned problems for controlling an expiratory valve in a ventilator during expiration.

Another object of the invention is to provide a computer software product which e.g. can be used for upgrading existing ventilators and enabling them to perform the functions of in the inventive-method.

The above objects are achieved in accordance with the principles of the present invention in a method, and a computer software product downloadable into a control unit for programming the control unit to operate in accordance with the method, wherein the expiratory valve is maintained fully open in a first interval within an expiratory phase and, in this first interval, flow through and/or pressure at the expiratory valve are measured. The control unit determines if-and when this measured value satisfies a predetermined condition, and a second interval is begun within the expiratory phase if and when the measured value satisfies the predetermined condition. In the second interval, the expiratory valve is regulated to produce a predetermined end pressure in the expiratory section of the ventilator, with which the expiratory valve communicates.

When an expiratory valve is controllable, the valve can be kept fully open for a first interval and then be regulated towards the reference value (PEEP) during a second interval when expiration has largely subsided. Flow through the expiratory valve is determined and utilized for establishing when the; first interval should terminate and when the second interval should begin. In the alternative, the pressure at the expiratory valve is utilized in a similar manner.

It is also possible to utilize a combination of flow and pressure in the expiratory control.

Pressure in the inspiratory part of the ventilator also can be utilized together with flow to determine when to shift from the first interval to the second interval.

Determination of the transition from the first interval to the second interval is appropriately made from threshold values with which the measured flow, pressure or a combination of flow and pressure, is compared. The second interval begins when the threshold value is exceeded. A combination of flow and pressure could e.g. be a calculated estimate of lung pressure, based on measurement values and a model for the system. A threshold value for the estimated lung pressure is then used for determining the transition from the first interval to the second interval.

DESCRIPTION OF THE PREFERRED EMBODIMENTS

Figure 1:
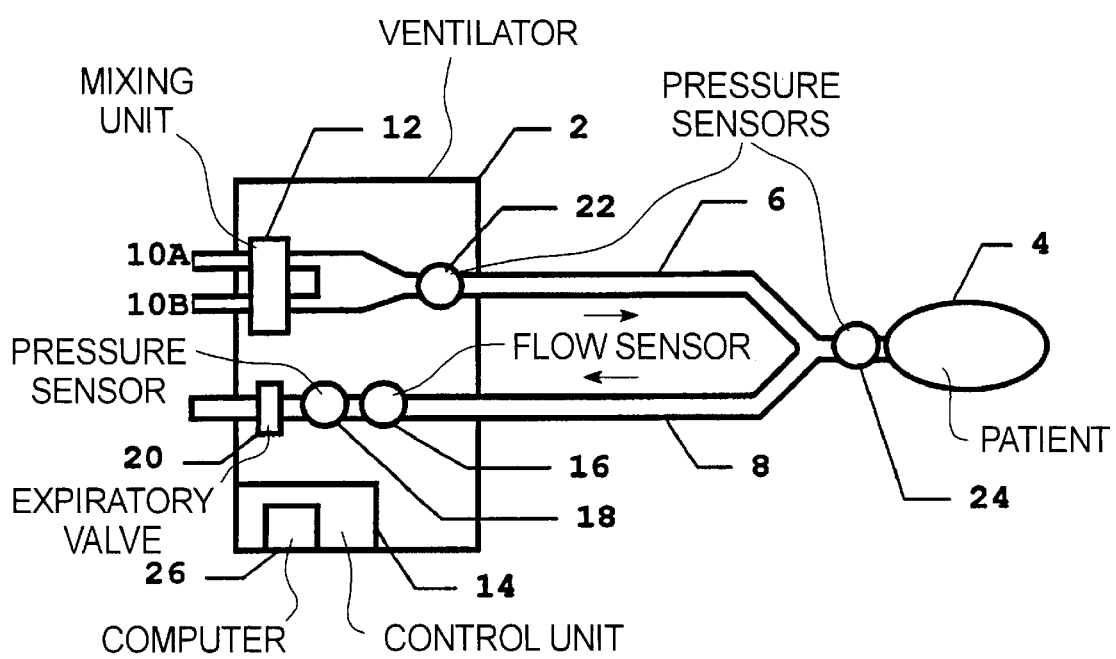
FIG. 1 is a schematic illustration of a ventilator in which the method according the invention can be implemented.

FIG. 1 shows a ventilator 2, connected to a patient 4, for providing respiratory care. During inspiration, breathing gas is carried to the patient 4 in an inspiratory line 6 and returns to the ventilator 2 in an expiratory line 8.

Breathing gas is a mixture of gases supplied to the ventilator 2 through a first gas connector 10A and a second gas connector 10B. A mixer unit 12 regulates the pressure and flow of the respective gas so the mixed breathing gas has the pressure and flow set by the physician. The mixer unit 12, which incorporates e.g. valves, is controlled by a control unit 14 in the ventilator 2. The mixer unit 12 can also be regulated to supply a continuous basic flow of breathing gas during expiration, in addition to inspiratory flow.

Expired breathing gas passes a flow sensor 16 and a first pressure sensor 18 in the expiratory section of the ventilator 2 before it is discharged into atmosphere through an expiratory valve 20. The measurement signals are sent to the control unit 14 that regulates the expiratory valve 20.

The regulatory unit 14 regulates the expiratory valve 20 in such a way that the expiratory valve 20 opens almost completely for a first period during expiration in order to minimize resistance to expiration. A second period then starts during which the expiratory valve 20 is regulated so a pre-set end pressure (PEEP) is achieved at the end of expiration. This end pressure consists of a positive pressure in relation to atmosphere and can vary from 0 cmH$_2$O and up.

In order to establish when the transition to the second interval should take place, the flow measured by the flow sensor 16 is utilized. The flow is indirectly related to the pressure in the lung of the patient 4. The pressure measured by the first pressure sensor 18 can be used in a similar way or in addition to the flow. Pressure in the inspiratory line 6, which can be measured with a second pressure sensor 22 can also be used as well as the pressure in the lungs. The latter parameter can be measured by a third pressure sensor 24. The third pressure sensor 24 is advantageously placed down in the patient's trachea, e.g. by the carina. The third pressure sensor can alternatively be located at the Y-piece (connecting the inspiratory line. 5 and the expiratory line 8 by the patient 4).

The determined flow can then be used alone or in combination with pressure by the control unit 14 for determining when regulation of the expiratory valve 20 should begin in order to achieve the correct end pressure (PEEP). The determination is made in dependency on a condition. The condition can be a threshold value for flow. The control unit 14 then compares the flow to with threshold value, and the second interval and regulation of the expiratory vale 20 start when the measurement signal reaches the threshold value.

The control unit 14 contains a computer 26 for running the software required for performing the method according to the invention. The computer 26 has an internal memory for storage of program components for performing the method. Alternatively, the computer 26 can be a separate unit that can be connected to the control unit 14 for performing the method. Software for the computer 26 can be stored on a suitable medium, such as a CD-ROM disk, as well as in internal memory. Upgrading existing ventilators to enable them to perform the method could then be achieved by transferring software from the CD-ROM disk to the computer's 26 internal memory. Alternatively, the CD-ROM disk could be used as internal memory for the computer 26.

FIGS. 2–5 show how flow and pressure can be used in determining when transition from the first interval to the second should take place.

Figure 2:
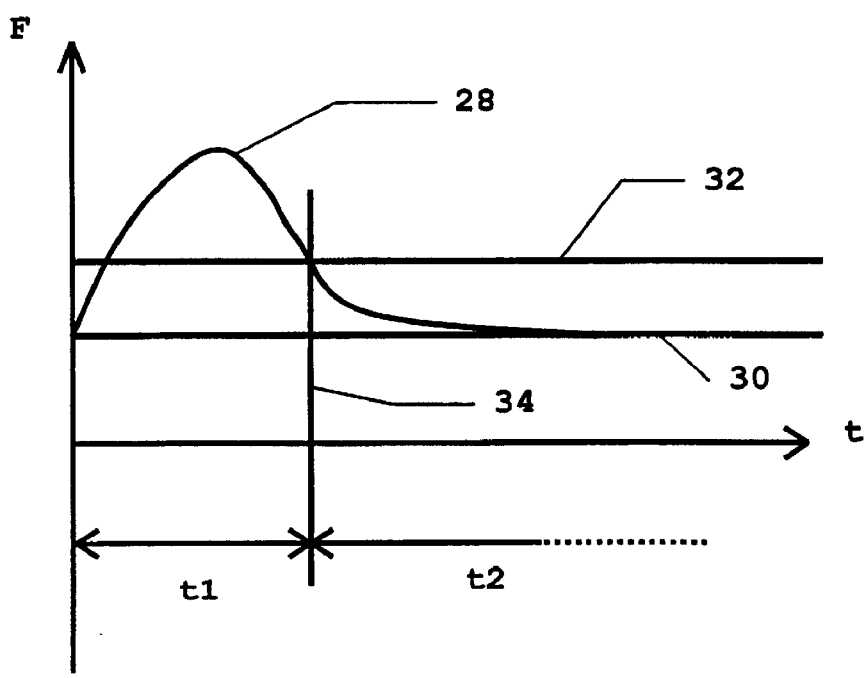
FIG. 2 is a diagram illustrating the use of flow in the method according to the invention.

FIG. 2 shows flow as a function of time during expiration. Here, flows are shown as positive, even if the nomenclature usually designates flows to the patient as positive and flows from the patient as negative. A flow curve 28 shows one possible course of events for flow during expiration in relation to the method according to the invention. A first horizontal line 30 depicts a basic -flow in both the inspiratory line and the expiratory line during expiration.

The purpose of the basic flow 30 is to facilitate the triggering of inspiratory phases in spontaneous breathing. In principle, therefore, the basic flow 30 can be imposed at any time during the expiratory phase, e.g. at the end. The imposition of the basic flow 30 can also suitably occur in conjunction with the transition from the first interval t1 to the second interval t2. FIG. 2 depicts basic flow 30 right from the start of expiration in order to facilitate an understanding of the method according to the invention.

The flow curve 28 first rises and passes, a peak at which outflow is at a maximum. The flow then abates, which is the part of the flow curve 28 of particular interest in the inventive method. A second horizontal line 32 shows a threshold value for flow. A transition to the second interval t2 takes place when measured flow (flow curve 28) exceeds the threshold value 32.

Thus, a vertical line 34 designates the end of the first interval t1, during which the expiratory valve is almost completely open, and the second interval t2, during which the expiratory valve is regulated so the pre-set end pressure is achieved, starts. The duration of the second interval t2 is mainly determined by the difference between the expiration duration set and t1.

In all normal circumstances, this method provides enough time to achieve the correct end pressure. The threshold value 32 can be set as a fixed level above the basic flow 30, a percentile level above the basic flow 30, a fixed level above a zero flow, an adjustable level (above zero or basic flow) or it can be set by the control unit from e.g. pressure conditions in the inspiratory and expiratory lines.

Figure 3:
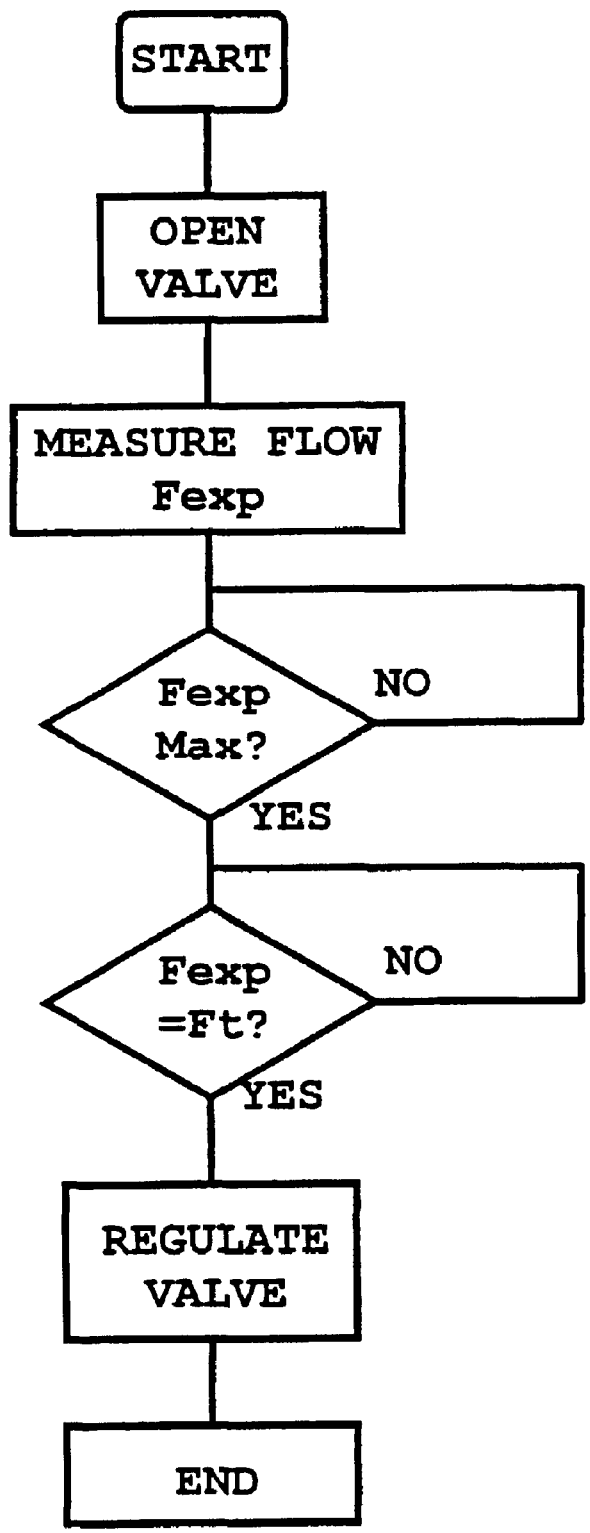
FIG. 3 is a flow chart showing a possible programming sequence for a computer software product.

Execution of the method with software is illustrated in the flow chart in FIG. 3.

Expiration begins with the first interval in the START block, and the expiratory valve is almost completely open (OPEN VALVE). Flow through the expiratory line is measured (MEASURE FLOW). Since the threshold value will be exceeded as soon as expiratory flow starts, the program first senses whether flow maxima have been reached (Fexp Max?). When this is the case (YES), the flow is compared to the threshold value (Fexp=Ft?). When flow exceeds the threshold value, the second interval starts, and the expiratory valve is regulated so the correct end pressure is obtained (REGULATE VALVE). Finally, this part of the program is concluded (when the correct PEEP has been reached), and a new program component can begin.

As noted above, flow need not be used alone for determining the transition from the first to the second interval.

Pressure in the inspiratory line can be used in addition. The diagram in FIG. 4 illustrates the way in which this pressure can be used together with flow for controlling the transition from the first interval t1 to the second interval t2.

Figure 4:
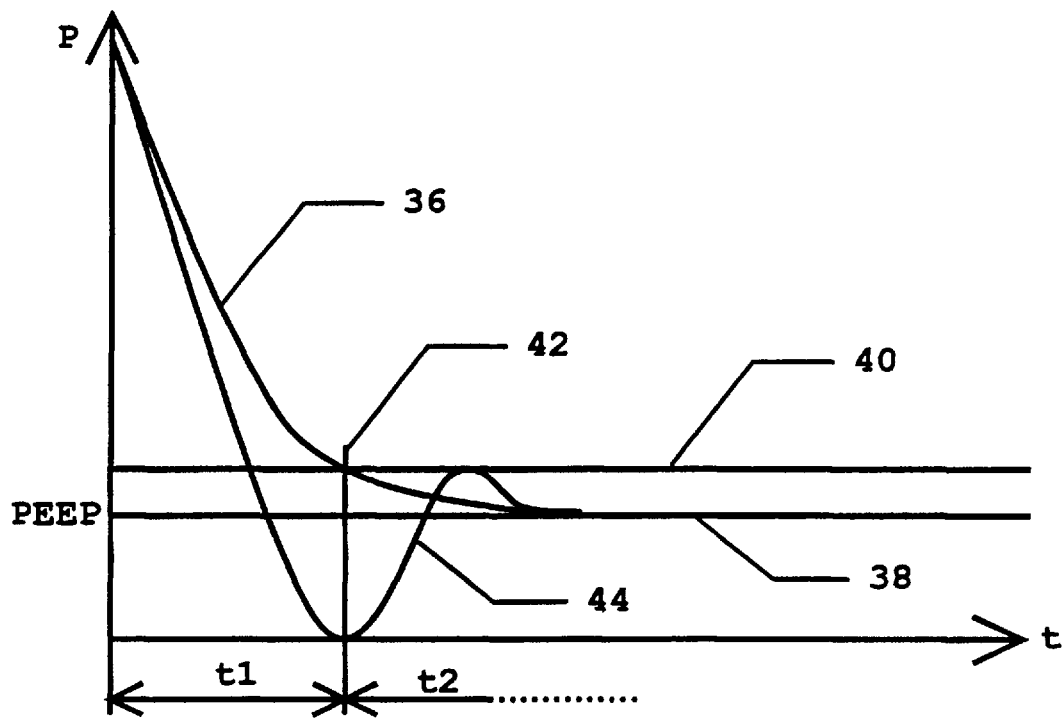
FIG. 4 is a diagram of a first example of the additional use of pressure as in the method according to the invention.

FIG. 4 is a pressure-time diagram. A first pressure curve 36 depicts a calculated or estimated pressure in the lungs. This estimate is based on a model for the entire system. Flow and pressure are suitable parameters for the calculation. PEEP is shown as line 38. The condition here is a pressure value 40 for the estimated lung pressure. Expiration starts in the first interval t1. When the estimated lung pressure 36 crosses the threshold 40, regulation of the valve in the second interval t2 commences. This is shown with vertical line 42.

The diagram also shows a second pressure curve 44 that corresponds to pressure at the expiratory valve during expiration. This pressure virtually drops to atmospheric pressure. For this reason, it might be assumed that pressure at the expiratory valve is an unusable parameter. However, FIG. 5 shows how it can be used.

Here, a first pressure curve 46 constitutes;the pressure in the expiratory line. The level of PEEP is depicted with a first horizontal line 48 and the threshold value with a second horizontal line 50. Here, the threshold value 50 is less than the PEEP level 48. When the first pressure curve 46 reaches the threshold value 50, regulation switches from the first interval t1 to the second interval t2.

Figure 5:
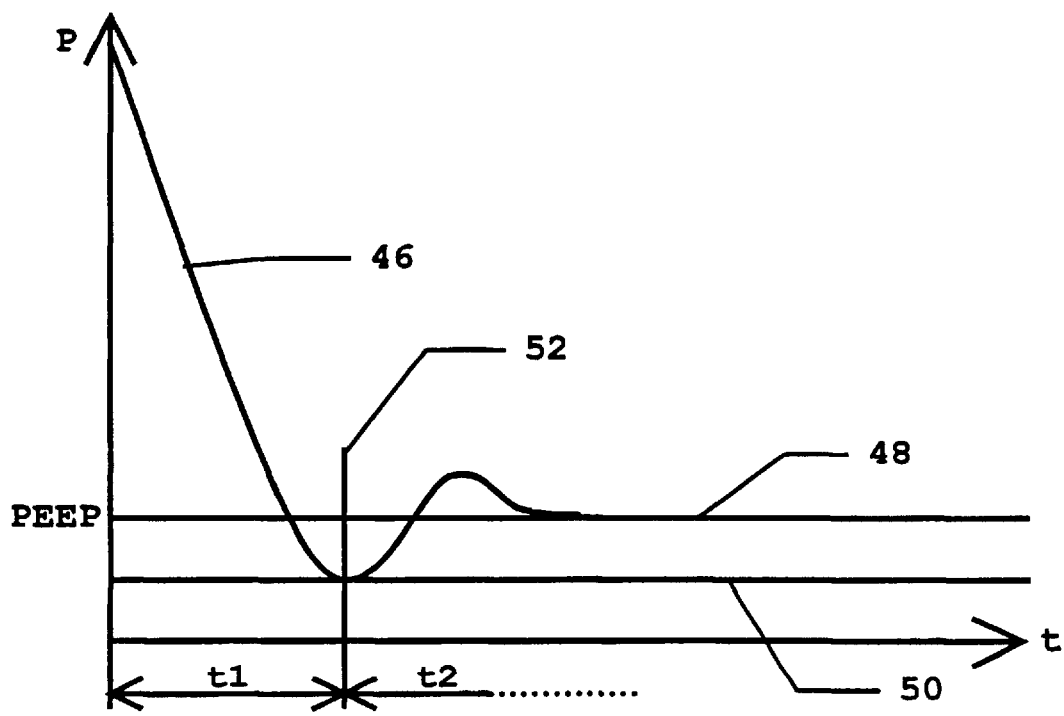
FIG. 5 is a diagram of the use of pressure at the expiratory valve as a parameter in the method according to the invention.

The threshold values in FIGS. 4 and 5 can, in the corresponding way as for the threshold value in FIG. 2, be fixed values (in relation to PEEP or absolute pressure), can be adjustable, or can be determined (or adapted), by means of functions, in the control unit.

For example, an adaptive change in threshold values can be made from the relationship between the duration of the first interval t1 and the second interval t2 in one or a number of preceding breathing cycles.

FIG. 1 only shows one type of ventilator with which the method according to the invention can be used. Here "ventilator" also refers to other devices for supplying breathing gas, e.g. respirators and anaesthesia machines.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for controlling an expiratory valve in a ventilator during an expiratory phase, comprising:

maintaining said expiratory valve substantially fully open for a first interval within said expiratory phase;

in said first interval, measuring at least one parameter selected from the group consisting of flow through said expiratory valve and pressure at said expiratory valve;

determining if and when said at least one parameter satisfies a predetermined condition;

beginning a second interval within said expiratory phase if and when said at least one parameter satisfies said predetermined condition; and regulating said expiratory valve during said second interval to produce a predetermined end pressure in an expiratory section of said ventilator with which said expiratory valve communicates.

2. A method as claimed in claim 1 comprising employing a threshold value as said predetermined condition.

3. A method as claimed in claim 1 wherein said at least one parameter comprises pressure at said expiratory valve, and employing a threshold value for said pressure at said expiratory valve as said predetermined condition.

4. A method as claimed in claim 1 comprising the additional step of additionally measuring pressure in an inspiratory section of said ventilator an employing measurement of said pressure in said inspiratory section to determine if and when said predetermined condition is satisfied.

5. A method as claimed in claim 1 comprising calculating an estimate of pressure in the lungs of a subject who produces said expiratory phase, and employing said calculated estimate as said predetermined condition.

6. In a ventilator having a computerized control unit, an expiratory section containing an expiratory valve, a flow sensor for measuring flow through said expiratory valve, and a pressure sensor for measuring pressure at said expiratory valve, said computerized control unit being connected to said expiratory valve, said flow sensor and said pressure sensor, the improvement comprising:

a computer software product programmed into said computerized control unit which, when programmed into said computerized control unit, programs said computerized control unit to control said expiratory valve to maintain said expiratory valve substantially fully open during a first interval in an expiratory phase and for, during said first interval, receiving a signal representing a parameter from at least one of said flow sensor and said pressure sensor, for making a determination of if and when said parameter satisfies a predetermined condition, and for beginning a second interval if and when said parameter satisfies said predetermined condition and for regulating said expiratory valve in said second interval to achieve a preset end pressure in said expiratory section.

* * * * *